United States Patent
Qi et al.

(10) Patent No.: US 11,852,526 B2
(45) Date of Patent: Dec. 26, 2023

(54) PRINTED SUN EXPOSURE SENSOR WITH FLUORESCENT TONER FOR DISPOSABLE/SINGLE USE

(71) Applicant: Xerox Corporation, Norwalk, CT (US)

(72) Inventors: Yu Qi, Penfield, NY (US); Eliud Robles Flores, Rochester, NY (US); Judith Millner Vandewinckel, Livonia, NY (US); Andrew Beams, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 36 days.

(21) Appl. No.: 17/114,669

(22) Filed: Dec. 8, 2020

(65) Prior Publication Data
US 2022/0178742 A1    Jun. 9, 2022

(51) Int. Cl.
  *G01J 1/42*   (2006.01)
  *G01J 1/58*   (2006.01)
  *G01N 21/64*  (2006.01)
  *A61B 5/00*   (2006.01)

(52) U.S. Cl.
  CPC .............. *G01J 1/429* (2013.01); *A61B 5/441* (2013.01); *G01J 1/58* (2013.01); *G01N 21/6428* (2013.01)

(58) Field of Classification Search
  CPC .. G01J 1/429; G01J 1/58; A61B 5/441; G01N 21/6428
  See application file for complete search history.

(56) References Cited

U.S. PATENT DOCUMENTS

| | | | |
|---|---|---|---|
| 4,863,282 A | | 9/1989 | Rickson |
| 4,935,326 A | * | 6/1990 | Creatura .............. G03G 9/1131 428/407 |
| 4,937,166 A | * | 6/1990 | Creatura .............. G03G 9/1131 428/407 |
| 5,387,798 A | * | 2/1995 | Funakoshi ............... C09K 9/02 250/474.1 |
| 5,612,541 A | * | 3/1997 | Hoffmann ................. G01J 1/50 250/474.1 |

(Continued)

OTHER PUBLICATIONS

Eliud Robles Flores, et al., U.S. Appl. No. 16/676,971, filed Nov. 7, 2019, "High Visibility Fluorescent Yellow Toner and Toner Process," not yet published.

(Continued)

*Primary Examiner* — David P Porta
*Assistant Examiner* — Djura Malevic
(74) *Attorney, Agent, or Firm* — Marylou J. Lavoie, Esq. LLC

(57) ABSTRACT

A sun exposure sensor for disposable or single use including a substrate having an upper surface and a lower surface; a sun exposure sensing portion disposed on the upper surface of the substrate, the sun exposure sensing portion comprising a fluorescent toner image, wherein the fluorescent toner image increasingly fades upon exposure to sunlight; a sun exposure scale disposed on the upper surface of the substrate, the sun exposure scale comprising an evaluation image for evaluating an amount of fading of the fluorescent toner image; an optional coating layer disposed over all or a portion of the upper surface of the substrate; an optional backing layer disposed over all or a portion of the lower surface of the substrate. A process for preparing the sensor using xerographic toner printing.

23 Claims, 4 Drawing Sheets

(56) References Cited

U.S. PATENT DOCUMENTS

| | | | | |
|---|---|---|---|---|
| 5,612,542 A * | 3/1997 | Brown | | G01J 1/50 |
| | | | | 250/474.1 |
| 5,691,158 A * | 11/1997 | Reece | | G01N 33/6881 |
| | | | | 435/7.92 |
| 5,916,541 A * | 6/1999 | Stewart | | A61K 8/922 |
| | | | | 424/59 |
| 5,986,273 A | 11/1999 | Tripp et al. | | |
| 6,046,455 A * | 4/2000 | Ribi | | G01J 1/50 |
| | | | | 250/336.1 |
| 6,063,827 A * | 5/2000 | Sacripante | | C08G 63/58 |
| | | | | 430/108.1 |
| 6,132,681 A | 10/2000 | Faran et al. | | |
| 6,531,118 B1 * | 3/2003 | Gonzalez | | A61K 8/49 |
| | | | | 424/400 |
| 6,818,904 B1 | 10/2004 | Ferren et al. | | |
| 8,835,643 B2 * | 9/2014 | Wang | | A61K 8/63 |
| | | | | 546/335 |
| 8,961,897 B2 | 2/2015 | Faran | | |
| 9,164,078 B2 * | 10/2015 | Min | | A61B 5/14535 |
| 9,211,247 B2 * | 12/2015 | Barrie | | A61K 8/34 |
| 9,963,271 B2 * | 5/2018 | Richter | | B65D 85/70 |
| 10,247,603 B2 * | 4/2019 | Hatta | | G01J 1/50 |
| 10,957,807 B2 * | 3/2021 | Kotru | | G01J 1/44 |
| 11,174,407 B2 * | 11/2021 | Gooding | | C09D 11/322 |
| 2002/0022008 A1 * | 2/2002 | Forest | | G01J 1/50 |
| | | | | 424/59 |
| 2003/0054277 A1 * | 3/2003 | Fujikura | | G03G 9/081 |
| | | | | 430/108.1 |
| 2003/0226978 A1 * | 12/2003 | Ribi | | A61K 8/02 |
| | | | | 250/474.1 |
| 2004/0233465 A1 * | 11/2004 | Coyle | | C09D 11/32 |
| | | | | 358/1.9 |
| 2005/0285050 A1 * | 12/2005 | Bruce | | G01J 1/429 |
| | | | | 250/474.1 |
| 2006/0001007 A1 * | 1/2006 | Fukui | | C09K 11/7706 |
| | | | | 252/301.5 |
| 2006/0011730 A1 * | 1/2006 | Bi | | C09D 11/037 |
| | | | | 235/487 |
| 2008/0110995 A1 * | 5/2008 | Iftime | | C09D 11/34 |
| | | | | 235/494 |
| 2008/0124498 A1 * | 5/2008 | Cole | | B41M 5/267 |
| | | | | 428/29 |
| 2008/0296513 A1 * | 12/2008 | Ribi | | G01J 1/50 |
| | | | | 250/474.1 |
| 2009/0104373 A1 * | 4/2009 | Vanbesien | | B41M 7/02 |
| | | | | 427/157 |
| 2009/0212115 A1 * | 8/2009 | Iftime | | G06K 1/121 |
| | | | | 235/468 |
| 2009/0214972 A1 * | 8/2009 | Wosnick | | G03G 9/0926 |
| | | | | 430/108.4 |
| 2010/0062360 A1 * | 3/2010 | Victor | | G03G 9/122 |
| | | | | 430/105 |
| 2010/0330487 A1 * | 12/2010 | Veregin | | G03G 9/08797 |
| | | | | 430/108.7 |
| 2011/0293908 A1 * | 12/2011 | Jeganathan | | C09K 9/02 |
| | | | | 427/160 |
| 2011/0300572 A1 * | 12/2011 | Dueva-Koganov | | G01N 33/15 |
| | | | | 435/287.1 |
| 2012/0288690 A1 * | 11/2012 | Forsythe | | C09K 9/02 |
| | | | | 427/160 |
| 2014/0001377 A1 * | 1/2014 | Iftime | | C09D 11/50 |
| | | | | 252/301.16 |
| 2014/0038305 A1 * | 2/2014 | Sharavara | | G01N 21/78 |
| | | | | 436/164 |
| 2014/0197364 A1 * | 7/2014 | Richards-Johnson | | |
| | | | | C09K 11/06 |
| | | | | 252/301.35 |
| 2014/0348757 A1 * | 11/2014 | Barrie | | A61K 8/046 |
| | | | | 424/59 |
| 2015/0253252 A1 * | 9/2015 | Smyth | | G01N 21/77 |
| | | | | 422/429 |
| 2015/0355021 A1 * | 12/2015 | Hatta | | G01J 1/0407 |
| | | | | 427/160 |
| 2019/0002720 A1 * | 1/2019 | Gooding | | G01N 3/22 |
| 2019/0284406 A1 * | 9/2019 | Levine | | A61K 8/8152 |
| 2021/0141318 A1 * | 5/2021 | Flores | | G03G 15/0131 |

OTHER PUBLICATIONS

Khiabani, et al., "Paper-Based Sensor for Monitoring Sun Exposure," ACS Sens., May 16, 2016, 1, 775-780.

Extended European Search Report issued in European Application No. 21210616.5-1020, dated Apr. 20, 2022.

Anonymous, "Food Dyes Can Function as Probes to Improve Food Quality," Feb. 15, 2015, https://www.foodingredientsfirst.com/news/food-dyes-can-function-as-probes-to-improve-food-quality.html.

* cited by examiner

| Toner Example | Light exposure (min) | | |
|---|---|---|---|
| | 0 | 120 | 240 |
| 7 | | | |
| 8 | | | |
| 9 | | | |
| 10 | | | |
| 12 | | | |

FIG. 4

PRINTED SUN EXPOSURE SENSOR WITH FLUORESCENT TONER FOR DISPOSABLE/SINGLE USE

BACKGROUND

Disclosed herein is a sun exposure sensor for disposable or single use comprising a substrate having an upper surface and a lower surface; a sun exposure sensing portion disposed on the upper surface of the substrate, the sun exposure sensing portion comprising a fluorescent toner image, wherein the fluorescent toner image increasingly fades upon exposure to sunlight; a sun exposure scale disposed on the upper surface of the substrate, the sun exposure scale comprising an evaluation image for evaluating an amount of fading of the fluorescent toner image; an optional coating layer disposed over all or a portion of the upper surface of the substrate; an optional backing layer disposed over all or a portion of the lower surface of the substrate.

Also disclosed is a process for preparing a sun exposure sensor, the process comprising: providing a substrate having an upper surface and a lower surface; disposing a sun exposure sensing portion on the upper surface of the substrate, the sun exposure sensing portion comprising a fluorescent toner image, wherein the fluorescent toner image increasingly fades upon exposure to sunlight; disposing a sun exposure scale on the upper surface of the substrate, the sun exposure scale comprising an evaluation image for evaluating an amount of fading of the fluorescent toner image; optionally, disposing a coating layer over all or a portion of the upper surface of the substrate; optionally, disposing a backing layer disposed over all or a portion of the lower surface of the substrate.

Most currently available ultra-violet (UV) radiation sensors require high-tech, complex devices to operate, such as smartphones or wearable smart technology. Recently, single-use, disposable sunburn sensors have come onto the market. One such sun exposure sensor reported in ACS (American Chemical Society) was created by inkjet printing titanium dioxide and food dye on paper. When enough UV radiation hits the sensor, titanium dioxide causes the dye to change color, notifying people of the large amount of sun exposure and warning them to get out of the sun or apply more sunscreen. See, Khiabani, et al., "Paper-Based Sensor For Monitoring Sun Exposure," ACS Sens., 2016, 1, 775-780, which is hereby incorporated by reference herein in its entirety.

While currently available sun exposure sensors may be suitable for their intended purposes, a need remains for improved sun exposure sensors, particularly for use by those who work outside or as a consumer/safety product for those who spend time enjoying the outdoors. Further, a need remains for an improved sun exposure sensor that is simple to prepare, easy to use, and inexpensive.

The appropriate components and process aspects of the each of the foregoing U.S. Patents and Patent Publications may be selected for the present disclosure in embodiments thereof. Further, throughout this application, various publications, patents, and published patent applications are referred to by an identifying citation. The disclosures of the publications, patents, and published patent applications referenced in this application are hereby incorporated by reference into the present disclosure to more fully describe the state of the art to which this invention pertains.

SUMMARY

Described is a sun exposure sensor for disposable or single use comprising: a substrate having an upper surface and a lower surface; a sun exposure sensing portion disposed on the upper surface of the substrate, the sun exposure sensing portion comprising a fluorescent toner image, wherein the fluorescent toner image increasingly fades upon exposure to sunlight; a sun exposure scale disposed on the upper surface of the substrate, the sun exposure scale comprising an evaluation image for evaluating an amount of fading of the fluorescent toner image; an optional coating layer disposed over all or a portion of the upper surface of the substrate; an optional backing layer disposed over all or a portion of the lower surface of the substrate.

Also described is a process for preparing a sun exposure sensor, the process comprising: providing a substrate having an upper surface and a lower surface; disposing a sun exposure sensing portion on the upper surface of the substrate, the sun exposure sensing portion comprising a fluorescent toner image, wherein the fluorescent toner image increasingly fades upon exposure to sunlight; disposing a sun exposure scale on the upper surface of the substrate, the sun exposure scale comprising an evaluation image for evaluating an amount of fading of the fluorescent toner image; optionally, disposing a coating layer over all or a portion of the upper surface of the substrate; optionally, disposing a backing layer disposed over all or a portion of the lower surface of the substrate.

BRIEF DESCRIPTION OF THE DRAWINGS

FIG. 4 is an illustration of color change of different fluorescent prints in accordance with the present embodiments.

DETAILED DESCRIPTION

Figure 1:
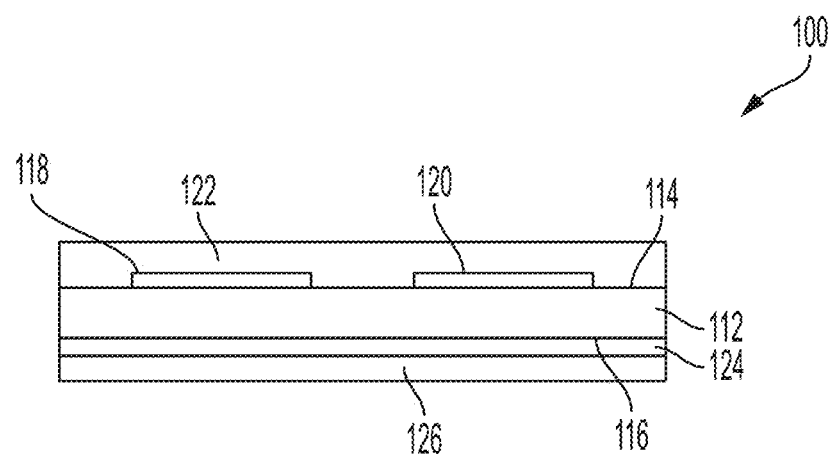
FIG. 1 is an illustration of a sun exposure sensor in accordance with the present embodiments.

A sun exposure sensor is provided that is easy to prepare, simple, and inexpensive. The entire sun exposure sensor can be printed in a single pass print job, using any office product capable of printing fluorescent toner kits, in embodiments using Xerox® printing technology, such as Versant®, and in certain specific embodiments, such as Xerox® iGen® printing technology. The sun exposure sensor can be prepared with many media types and have various finishing operations applied thereto. In embodiments, the sun exposure sensor is a single-use, disposable sun exposure sensor.

The present single-use, disposable sun exposure sensor is based on fluorescent toner prints. The sensor exploits the fading mechanism of the fluorescent print due to fluorescent dye/colorant decomposition under direct sunlight. The decoloration speed correlates to light exposure intensity. That is, the color chroma shifts when extending the exposure time during lightfastness investigations. The printed sensor herein shows a person how much sunlight he/she is exposed to when staying outdoors. The exposure can be correlated, for example, to an Arizona day.

The printed sensor herein is made by printing a fluorescent toner on a substrate to form a solid image, and next to the image, a sun exposure scale is printed with a regular (non-fluorescent) pigmented toner simulating the color that the fluorescent toner progressively fades to with increasing sun exposure. The printed scale is robust to sunlight. The sensor discolors when exposed to direct sunlight. The sun exposure level is easily found by comparing the faded sensor to the scale. In embodiments, the scale can be printed with fading indicators from 0 to 8 which correlates to fractions of an Arizona day. The sensor can be prepared with different colors and can be applied to various substrates in accordance with customer/end user preference. The substrate can be a disposable substrate such as an adhesive label, a wrist band, plastics, foils, fabrics, etc. If desired, an overcoat can be applied to the sensor to make it water proof and scratch resistant. The overcoat will not affect the function of the sensor. The sensor thus provided is simple, easy to use, and very inexpensive.

In embodiments, a sun exposure sensor for disposable or single use comprises: a substrate having an upper surface and a lower surface; a sun exposure sensing portion disposed on the upper surface of the substrate, the sun exposure sensing portion comprising a fluorescent toner image, wherein the fluorescent toner image increasingly fades upon exposure to sunlight; a sun exposure scale disposed on the upper surface of the substrate, the sun exposure scale comprising an evaluation image for evaluating an amount of fading of the fluorescent toner image; an optional coating layer disposed over all or a portion of the upper surface of the substrate; an optional backing layer disposed over all or a portion of the lower surface of the substrate.

The fluorescent toner image can be any suitable or desired shape or configuration. In embodiments, the fluorescent toner image comprises a solid printed image in the shape of a rectangle, a square, a circle, or any other desired shape.

The sun exposure scale evaluation image can be any suitable or desired image. In embodiments, the sun exposure scale comprises a series of numbered shapes, for example circles, from 0 to 8 with each circle illustrating progressive fading comparable to the fading of the fluorescent toner image upon increased sun exposure. In other embodiments, the sun exposure scale can comprise any suitable or desired image that can provide a reference point for evaluating the fading of the fluorescent image. For example, the sun exposure scale can be a progressively fading printed image corresponding to the color fade of the fluorescent toner image upon increased sun exposure. The sun exposure scale can include a number of discrete reference points or can be a progressively fading image.

FIG. 1 illustrates a side view of one possible embodiment of a sun exposure sensor in accordance with the present embodiments. The sun exposure sensor 100 shown in FIG. 1 includes a substrate 112 having an upper surface 114 and a lower surface 116. A fluorescent toner image 118 for sensing sun exposure is disposed on upper surface 114 of the substrate 112. Sun exposure scale/non-fading evaluation image 120 is disposed on upper surface 114 of the substrate 112 adjacent to the fluorescent toner image 118. Coating layer 122 is optionally disposed over the upper surface 114 of the substrate 112 covering the fluorescent toner image 118 and the evaluation image 120. Coating layer 112 may be a clear coating. In embodiments, the coating layer is a water-resistant overcoat layer. In embodiments, the coating layer is a scratch-resistant overcoat layer. In embodiments, the overcoat layer is a water-resistant and scratch-resistant overcoat layer. Any suitable or desired coating layer can be selected. Suitable coating layers included acrylic coatings known in the art. Suitable coatings can include, for example, Crystal Clear Acrylic coating spray from KRYLON®, Plutonium™ Clear Coat Gloss Spray, Rust-Oleum® Spray Paint, Aleene's® Spray Gloss Finish Acrylic Sealer.

An optional adhesive layer 124 is disposed on the lower surface 116 of the substrate 112. The optional adhesive layer can be any suitable or desired material including an adhesive, a hook and loop closure type material, or other means for adhering the sensor to a surface. The adhesive can be any of a wide variety of adhesives which are readily available including adhesives in common use in the medical industry. In embodiments, the backing layer is present and comprises a hook and loop layer, an adhesive layer, a gel pad, and combinations thereof.

In embodiments, the adhesive layer is not present and the substrate itself comprises a wearable piece such as a wristband, an item of clothing, and the like, or other substrate including those as described herein. Optionally, backing layer 126 is disposed to cover all or a portion of the lower surface 116 of the substrate 112. Alternately, in embodiments where the adhesive layer is present, backing layer 126 is disposed to cover all or a portion of the adhesive layer 124. The backing layer can be any suitable or desired layer to cover the bottom of the substrate or the adhesive layer. In embodiments, the backing layer comprises a layer of cellulose or plastic that can be peeled away from the adhesive layer 124 immediately prior to use.

Figure 2:
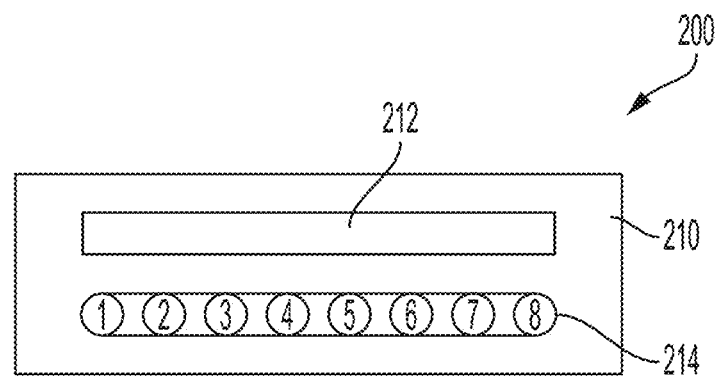
FIG. 2 is an illustration of an alternate embodiment of a sun exposure sensor in accordance with the present embodiments.

FIG. 2 illustrates a top view of a sensor in accordance with the present embodiments. The sensor 200 shown in FIG. 2 includes substrate 210. Fluorescent toner image 212 is printed on substrate 210. Sun exposure scale/evaluation image 214 is printed with regular, non-fluorescent toner on substrate 210 adjacent to the fluorescent toner image 212. An optional coating layer, not shown, can be disposed over the fluorescent toner image and the evaluation image to cover all or a portion of the substrate surface. Optional adhesive and backing layers, not shown, can be disposed on the substrate surface opposite to the sensor printed surface.

In embodiments, the sun exposure sensor can comprise two pieces. In embodiments, a sun exposure sensor for disposable or single use comprises: a first substrate having an upper surface and a lower surface; a sun exposure sensing portion disposed on the upper surface of the first substrate, the sun exposure sensing portion comprising a fluorescent toner image, wherein the fluorescent toner image increasingly fades upon exposure to sunlight; a second substrate having an upper surface and a lower surface; a sun exposure scale disposed on the upper surface of the second substrate, the sun exposure scale comprising an evaluation image for evaluating an amount of fading of the fluorescent toner image; an optional coating layer disposed over all or a portion of the upper surface of the first substrate; an optional coating layer disposed over all or a portion of the upper surface of the second substrate; an optional backing layer disposed over all or a portion of the lower surface of the first substrate; and an optional backing layer disposed over all or a portion of the lower surface of the second substrate.

Figure 3:
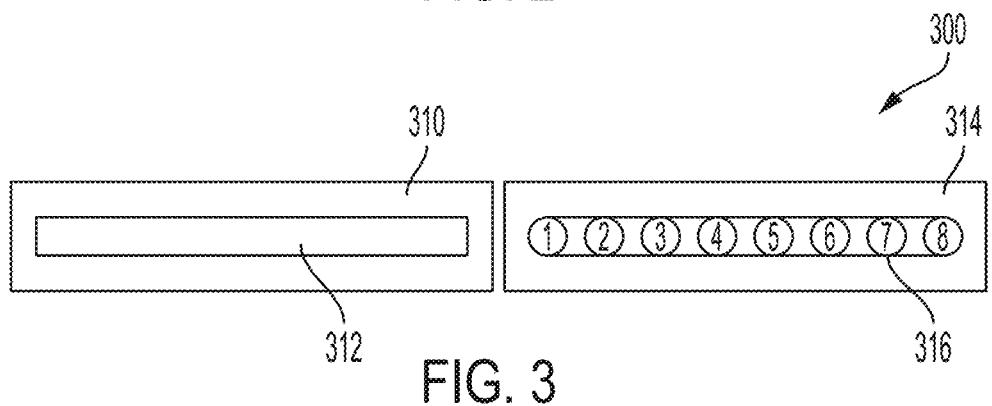
FIG. 3 is an illustration of an alternate embodiment of a sun exposure sensor in accordance with the present embodiments.

FIG. 3 illustrates a top view of a sensor in accordance with the present embodiments wherein the sun exposure sensing portion comprising the fluorescent toner image is disposed on a first substrate and the sun exposure scale evaluation image is disposed on a second, separate substrate. The sensor 300 shown in FIG. 3 includes substrate 310 including fluorescent toner image 312 printed on the substrate 310. Sun exposure scale/evaluation image 316 is printed with regular, non-fluorescent toner on a separate substrate 314. The materials comprising the substrate 310 and substrate 314 can be the same or different. In this embodiment, the sun exposure sensing portion comprising the substrate 310 printed with the fluorescent toner image 310 can be worn or disposed on a surface exposed to the sun and the evaluation portion comprising the scale 316 printed on the substrate 314 can be carried separately in a wallet or pocket or other place to be accessed as desired for comparing the fading of the fluorescent toner image 312 with the scale evaluation image 316. In this embodiment, the sun exposure sensor can be smaller overall due to the sun exposure sensor portion being separate from the evaluation portion.

The fluorescent toner image forming the sun exposure sensor portion can be prepared using any suitable or desired fluorescent toner. In embodiments, the sun exposure sensing portion fluorescent toner image is printed with a fluorescent toner covering a spectrum of reflectance from 400 nm to 700 nm. In embodiments, the sun exposure sensing portion fluorescent toner image is printed with a fluorescent toner selected from the group consisting of yellow fluorescent toner, magenta fluorescent toner, orange fluorescent toner, pink fluorescent toner, green fluorescent, red fluorescent toner, blue fluorescent toner, and combinations thereof.

In certain embodiments, the sun exposure sensing portion fluorescent toner image is printed with a fluorescent yellow toner.

In certain embodiment, the fluorescent toner selected is a high visibility fluorescent yellow toner as described in U.S. patent application Ser. No. 16/676,971, which is hereby incorporated by reference herein in its entirety. Thus, in certain specific embodiments, the sun exposure sensing portion fluorescent toner image is printed with a fluorescent yellow toner comprising: a core comprising a first solvent yellow 160-incorporated amorphous polyester; a second solvent yellow 160-incorporated amorphous polyester; wherein the first amorphous polyester and the second amorphous polyester are different; and a crystalline polyester; a shell disposed over the core, the shell comprising at least one amorphous polyester; wherein the toner provides printed images having an L* value of greater than 90, an a* value of from about less than −40 to about −20, and a b* value of greater than 75.

The fluorescent toners selected for the sensors herein can comprise resins, fluorescent colorant, optional wax, and other optional toner additives. The toner can optionally comprise a core-shell configuration. The toner resins can comprise a combination of amorphous resin and crystalline resin. In embodiments, the toner comprises a core-shell configuration wherein the core comprises a combination of amorphous and crystalline polyester and a shell comprises at least one amorphous polyester. In embodiments, the toner comprises a core-shell configuration wherein the core comprises a combination of first and second solvent yellow-160 incorporated amorphous resins and a crystalline polyester (crystalline resin not incorporated with solvent yellow 160) and a shell comprises at least one amorphous polyester as described in U.S. patent application Ser. No. 16/676,971.

Crystalline Resin.

The toner herein may include a crystalline resin. The crystalline resin herein may be a crystalline polyester resin formed by reacting a diol with a diacid in the presence of an optional catalyst. For forming a crystalline polyester, suitable organic diols include aliphatic diols with from about 2 to about 36 carbon atoms, such as 1,2-ethanediol, 1,3-propanediol, 1,4-butanediol, 1,5-pentanediol, 2,2-dimethyl-propane-1,3-diol, 1,6-hexanediol, 1,7-heptanediol, 1,8-octanediol, 1,9-nonanediol, 1,10-decanediol, 1,12-dodecanediol, combinations thereof, and the like, including their structural isomers. The aliphatic diol may be, for example, selected in an amount of from about 40 to about 60 mole percent of the resin, from about 42 to about 55 mole percent of the resin, or from about 45 to about 53 mole percent of the resin, and a second diol may be selected in an amount of from about 0 to about 10 mole percent of the resin or from about 1 to 4 mole percent of the resin.

Examples of organic diacids or diesters including vinyl diacids or vinyl diesters selected for the preparation of crystalline resins include oxalic acid, succinic acid, glutaric acid, adipic acid, suberic acid, azelaic acid, sebacic acid, fumaric acid, dimethyl fumarate, dimethyl itaconate, cis-1,4-diacetoxy-2-butene, diethyl fumarate, diethyl maleate, phthalic acid, isophthalic acid, terephthalic acid, naphthalene-2,6-dicarboxylic acid, naphthalene-2,7-dicarboxylic acid, cyclohexane dicarboxylic acid, malonic acid and mesaconic acid, a diester or anhydride thereof. The organic diacid may be selected in an amount of, for example, from about 40 to about 60 mole percent of the resin, from about 42 to about 52 mole percent of the resin, or from about 45 to about 50 mole percent of the resin, and a second diacid can be selected in an amount of from about 0 to about 10 mole percent of the resin.

Polycondensation catalysts which may be utilized in forming crystalline (as well as amorphous) polyesters include tetraalkyl titanates, dialkyltin oxides such as dibutyltin oxide, tetraalkyltins such as dibutyltin dilaurate, and dialkyltin oxide hydroxides such as butyltin oxide hydroxide, aluminum alkoxides, alkyl zinc, dialkyl zinc, zinc oxide, stannous oxide, or combinations thereof. Such catalysts may be utilized in amounts of, for example, from about 0.01 mole percent to about 5 mole percent based on the starting diacid or diester used to generate the polyester resin.

Examples of crystalline resins include polyesters, polyamides, polyimides, polyolefins, polyethylene, polybutylene, polyisobutyrate, ethylene-propylene copolymers, ethylene-vinyl acetate copolymers, polypropylene, mixtures thereof, and the like. Specific crystalline resins may be polyester based, such as poly(ethylene-adipate), poly(propylene-adipate), poly(butylene-adipate), poly(pentylene-adipate), poly(hexylene-adipate), poly(octylene-adipate), poly(ethylene-succinate), poly(propylene-succinate), poly(butylene-succinate), poly(pentylene-succinate), poly(hexylene-succinate), poly(octylene-succinate), poly(ethylene-sebacate), poly(propylene-sebacate), poly(butylene-sebacate), poly(pentylene-sebacate), poly(hexylene-sebacate), poly(octylene-sebacate), poly(decylene-sebacate), poly(decylene-decanoate), poly(ethylene-decanoate), pol (ethylene dodecanoate), poly(nonylene-sebacate), poly(nonylene-decanoate), copoly(ethylene-fumarate)-copoly(ethylene-sebacate), copoly(ethylene-fumarate)-copoly(ethylene-decanoate), copoly(ethylene-fumarate)-copoly(ethylene-dodecanoate), copoly(2,2-dimethylpropane-1,3-diol-decanoate)-copoly(nonylene-decanoate), poly(octylene-adipate), and mixtures thereof. Examples of polyamides include poly(ethylene-adipamide), poly(propylene-adipamide), poly(butylene-adipamide), poly (pentylene-adipamide), poly(hexylene-adipamide), poly(octylene-adipamide), poly(ethylene-succinimide), poly(propylene-sebecamide), and mixtures thereof. Examples of polyimides include poly(ethylene-adipimide), poly(propylene-adipimide), poly(butylene-adipimide), poly(pentylene-adipimide), poly(hexylene-adipimide), poly(octylene-adipimide), poly(ethylene-succinimide), poly(propylene-succinimide), poly(butylene-succinimide), and mixtures thereof.

In embodiments, the crystalline polyester is of the formula

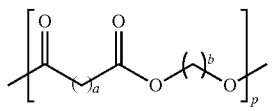

wherein each of a and b may range from 1 to 12, from 2 to 12, or from 4 to 12, and further wherein p may range from 10 to 100, from 20 to 80, or from 30 to 60. In embodiments, the crystalline polyester is poly(1,6-hexylene-1,12-dodecanoate), which may be generated by the reaction of dodecanedioc acid and 1,6-hexanediol.

The designation, "CX:CY," "CX:Y," "X:Y," and forms thereof as used herein describe crystalline resins, wherein C is carbon, X is a positive, non-zero integer identifying the number of methylene groups of the acid/ester monomer used to produce the crystalline polyester (CPE) and Y is a positive, non-zero integer identifying the number of methylene groups of the alcohol monomer used to produce the CPE. Thus, for example, C10 can represent, for example, a dodecanedioic acid and C6 can represent, for example, a hexanediol. X and Y each is 10 or lower. In embodiments, the sum of X and Y is 16 or lower. In certain embodiments, the sum and X and Y is 14 or lower.

In embodiments, the crystalline polyester is a C10:9 resin comprising polyester made from dodecanedioic acid (C10) and 1,9-nonanediol (C9).

As noted above, the crystalline polyesters may be prepared by a polycondensation process by reacting suitable organic diols and suitable organic diacids in the presence of polycondensation catalysts. A stoichiometric equimolar ratio of organic diol and organic diacid may be utilized, however, in some instances where the boiling point of the organic diol is from about 180° C. to about 230° C., an excess amount of diol, such as ethylene glycol or propylene glycol, of from about 0.2 to 1 mole equivalent, can be utilized and removed during the polycondensation process by distillation. The amount of catalyst utilized may vary, and can be selected in amounts, such as for example, from about 0.01 to about 1 or from about 0.1 to about 0.75 mole percent of the crystalline polyester resin.

The crystalline resin may be present in any suitable or desired amount. In embodiments, the crystalline resin may be present, for example, in an amount of from about 1% to about 85% by weight of the toner, from about 5% to about 50% by weight of the toner, or from about 10% to about 35% by weight of the toner.

The crystalline resin can possess various melting points of, for example, from about 30° C. to about 120° C., from about 50° C. to about 90° C. or from about 60° C. to about 80° C. The crystalline resin may have a number average molecular weight (Mn), as measured by gel permeation chromatography (GPC) of, for example, from about 1,000 to about 50,000, from about 2,000 to about 25,000, or from about 5,000 to about 20,000, and a weight average molecular weight (Mw) of, for example, from about 2,000 to about 100,000, from about 3,000 to about 80,000, or from about 10,000 to about 30,000, as determined by GPC. The molecular weight distribution (Mw/Mn) of the crystalline resin may be, for example, from about 2 to about 6, from about 3 to 15 about 5, or from about 2 to about 4.

Amorphous Resin.

The toner herein can be an amorphous resin. The amorphous resin may be an amorphous polyester resin formed by reacting a diol with a diacid in the presence of an optional catalyst. Examples of diacids or diesters including vinyl diacids or vinyl diesters utilized for the preparation of amorphous polyesters and include dicarboxylic acids or diesters such as terephthalic acid, phthalic acid, isophthalic acid, fumaric acid, trimellitic acid, dimethyl fumarate, dimethyl itaconate, cis-1,4-diacetoxy-2-butene, diethyl fumarate, diethyl maleate, maleic acid, succinic acid, itaconic acid, succinic acid, succinic anhydride, dodecylsuccinic acid, dodecylsuccinic anhydride, glutaric acid, glutaric anhydride, adipic acid, pimelic acid, suberic acid, azelaic acid, dodecanediacid, dimethyl terephthalate, diethyl terephthalate, dimethylisophthalate, diethylisophthalate, dimethylphthalate, phthalic anhydride, diethylphthalate, dimethylsuccinate, dimethylfumarate, dimethylmaleate, dimethylglutarate, dimethyladipate, dimethyl dodecylsuccinate, and combinations thereof. The organic diacids or diesters may be present, for example, in an amount from about 40 to about 60 mole percent of the resin, from about 42 to about 52 mole percent of the resin, or from about 45 to about 50 mole percent of the resin.

Examples of diols which may be utilized in generating an amorphous polyester include 1,2-propanediol, 1,3-propanediol, 1,2-butanediol, 1,3-butanediol, 1,4-butanediol, pentanediol, hexanediol, 2,2-dimethylpropanediol, 2,2,3-trimethylhexanediol, heptanediol, dodecanediol, bis (hydroxyethyl)-bisphenol A, bis(2-hydroxypropyl)-bisphenol A, 1,4-cyclohexanedimethanol, 1,3-cyclohexanedimethanol, xylenedimethanol, cyclohexanediol, diethylene glycol, bis(2-hydroxyethyl) oxide, dipropylene glycol, dibutylene, and combinations thereof. The amount of organic diols selected may vary, for example, the organic diols may be present in an amount from about 40 to about 60 mole percent of the resin, from about 42 to about 55 mole percent of the resin, or from about 45 to about 53 mole percent of the resin.

Examples of suitable amorphous resins include polyesters, polyamides, polyimides, polyolefins, polyethylene, polybutylene, polyisobutyrate, ethylene-propylene copolymers, ethylene-vinyl acetate copolymers, polypropylene, and the like, and mixtures thereof.

An unsaturated amorphous polyester resin may be utilized as a resin. Examples of such resins include those disclosed in U.S. Pat. No. 6,063,827, the disclosure of which is hereby incorporated by reference in its entirety. Exemplary unsaturated amorphous polyester resins include, but are not limited to, poly(propoxylated bisphenol co-fumarate), poly(ethoxylated bisphenol co-fumarate), poly(butyloxylated bisphenol co-fumarate), poly(co-propoxylated bisphenol co-ethoxylated bisphenol co-fumarate), poly(1,2-propylene fumarate), poly(propoxylated bisphenol co-maleate), poly(ethoxylated bisphenol co-maleate), poly(butyloxylated bisphenol co-maleate), poly(co-propoxylated bisphenol co-ethoxylated bisphenol co-maleate), poly(1,2-propylene maleate), poly (propoxylated bisphenol co-itaconate), poly(ethoxylated bisphenol co-itaconate), poly(butyloxylated bisphenol co-itaconate), poly(co-propoxylated bisphenol co-ethoxylated bisphenol co-itaconate), poly(1,2-propylene itaconate), and combinations thereof.

A suitable polyester resin may be an amorphous polyester such as a poly(propoxylated bisphenol A co-fumarate) resin. Examples of such resins and processes for their production include those disclosed in U.S. Pat. No. 6,063,827, the disclosure of which is hereby incorporated by reference in its entirety.

Suitable polyester resins include amorphous acidic polyester resins. An amorphous acid polyester resin may be based on any combination of propoxylated bisphenol A, ethoxylated bisphenol A, terephthalic acid, fumaric acid, and dodecenyl succinic anhydride, such as poly(propoxylated bisphenol-co-terephthlate-fumarate-dodecenylsuccinate). Another amorphous acid polyester resin which may be used is poly(propoxylated-ethoxylated bisphenol-co-terephthalate-dodecenylsuccinate-trimellitic anhydride).

An example of a linear propoxylated bisphenol A fumarate resin which may be utilized as a resin is available under the trade name SPAMII from Resana S/A Industrias Quimicas, Sao Paulo Brazil. Other propoxylated bisphenol A fumarate resins that may be utilized and are commercially available include GTUF and FPESL-2 from Kao Corporation, Japan, and EM181635 from Reichhold, Research Triangle Park, N.C., and the like.

An amorphous resin or combination of amorphous resins may be present, for example, in an amount of from about 5% to about 95% by weight of the toner, from about 30% to about 90% by weight of the toner, or from about 35% to about 85% by weight of the toner.

The amorphous resin or combination of amorphous resins may have a glass transition temperature of from about 30° C. to about 80° C., from about 35° C. to about 70° C., or from about 40° C. to about 65° C. The glass transition temperature may be measured using differential scanning calorimetry (DSC). The amorphous resin may have a Mn as measured by GPC of, for example, from about 1,000 to about 50,000, from about 2,000 to about 25,000, or from about 1,000 to about 10,000, and a Mw of, for example, from about 2,000 to about 100,000, from about 5,000 to about 90,000, from about 10,000 to about 90,000, from about 10,000 to about 30,000, or from about 70,000 to about 100,000, as determined by GPC.

One, two, or more resins may be used. Where two or more resins are used, the resins may be in any suitable ratio (e.g., weight ratio) such as for instance, of from about 1% (first resin)/99% (second resin) to about 99% (first resin)/1% (second resin), from about 10% (first resin)/90% (second resin) to about 90% (first resin)/10% (second resin). Where the resins include a combination of amorphous and crystalline resins, the resins may be in a weight ratio of, for example, from about 1% (crystalline resin)/99% (amorphous resin) to about 99% (crystalline resin)/1% (amorphous resin), or from about 10% (crystalline resin)/90% (amorphous resin) to about 90% (crystalline resin)/10% (amorphous resin). In some embodiments, the weight ratio of the resins is from about 80% to about 60% of the amorphous resin and from about 20% to about 40% of the crystalline resin. In such embodiments, the amorphous resin may be a combination of amorphous resins, e.g., a combination of two amorphous resins.

Fluorescent Toner.

In certain embodiments, the amorphous resin comprises a solvent yellow 160-incorporated amorphous resin as described in U.S. patent application Ser. No. 16/676,971.

In certain embodiments, the fluorescent toner is a fluorescent yellow toner comprising a core comprising a first solvent yellow 160-incorporated amorphous polyester; a second solvent yellow 160-incorporated amorphous polyester; wherein the first amorphous polyester and the second amorphous polyester are different; and a crystalline polyester; a shell disposed over the core, the shell comprising at least one amorphous polyester; wherein the toner provides printed images having an L* value of greater than 90, an a* value of from about less than −40 to about −20, and a b*value of greater than 75 as described in U.S. patent application Ser. No. 16/676,971. The fluorescent yellow colorant, when combined with the amorphous polyesters result in a toner which provides certain unique L* a* b* coordinates. The colorant can be solvent yellow 160 and its derivatives. In embodiments, the colorant is selected from the group consisting of solvent yellow 160, solvent yellow 160:1, and combinations thereof. In specific embodiments, the colorant is solvent yellow 160. In specific embodiments, the colorant is solvent yellow 160:1. The fluorescent yellow colorant is combined with the first amorphous polyester in a latex containing the fluorescent yellow colorant and the first amorphous polyester which latex is then used to form the toner. The fluorescent yellow colorant is combined with the second amorphous polyester in a latex containing the fluorescent yellow colorant and the second amorphous latex which latex is then used to form the toner.

Non-Fluorescent Toner.

The regular, non-fluorescent toner used to prepare the scale portion of the present sensor can be any suitable or desired toner. The toner may optionally have a core-shell configuration. The toner may include a resin or combination of resins including the resins described hereinabove for the fluorescent toner.

Colorants selected for the regular, non-fluorescent toner in accordance with the present disclosure include pigments, dyes, mixtures of pigments and dyes, mixtures of pigments, mixtures of dyes, and the like. The colorant may be, for example, carbon black, cyan, yellow, magenta, red, orange, brown, green, blue, violet, or mixtures thereof.

In embodiments wherein the colorant is a pigment, the pigment may be, for example, carbon black, phthalocyanines, quinacridones or RHODAMINE B™ type, red, green, orange, brown, violet, yellow, and the like.

Toner Preparation.

The fluorescent toner and the regular, non-fluorescent toner can be formed by any suitable or desired method as known in the art. In embodiments, any of the resins described above may be provided as an emulsion(s), e.g., by using a solvent-based phase inversion emulsification process. The emulsions may then be utilized as the raw materials to form the toners, e.g., by using an emulsion aggregation and coalescence (EA) process.

Wax.

Optionally, a wax may also be combined with the fluorescent or non-fluorescent colorant and the resin(s) in forming toner particles. The wax may be provided in a wax dispersion, which may comprise a single type of wax or a mixture of two or more different waxes. A single wax may be added, for example, to improve particular toner properties, such as toner particle shape, presence and amount of wax on the toner particle surface, charging and/or fusing characteristics, gloss, stripping, off-set properties, and the like. Alternatively, a combination of waxes can be added to provide multiple properties to the toner composition.

When included, the wax may be present in an amount of, for example, from about 1% to about 25% by weight of the toner or from about 5% to about 20% by weight of the toner particles.

Waxes that may be selected include waxes having, for example, an average molecular weight of from about 500 to about 20,000 or from about 1,000 to about 10,000. Waxes that may be used include, for example, polyolefins such as polyethylene including linear polyethylene waxes and branched polyethylene waxes, polypropylene including linear polypropylene waxes and branched polypropylene waxes, polymethylene waxes, polyethylene/amide, polyethylenetetrafluoroethylene, polyethylenetetrafluoroethylene/amide, and polybutene waxes such as commercially available from Allied Chemical and Petrolite Corporation, for example POLYWAX™ polyethylene waxes such as commercially available from Baker Petrolite, wax emulsions available from Michaelman, Inc. and the Daniels Products Company, EPOLENE N-15™ commercially available from Eastman Chemical Products, Inc., and VISCOL 550-P™, a low weight average molecular weight polypropylene available from Sanyo Kasei K. K.; plant-based waxes, such as carnauba wax, rice wax, candelilla wax, sumacs, jojoba oil; animal-based waxes, such as beeswax; mineral-based waxes and petroleum-based waxes, such as montan wax, ozokerite, ceresin, paraffin wax, microcrystalline wax such as waxes derived from distillation of crude oil, silicone waxes, mercapto waxes, polyester waxes, urethane waxes; modified polyolefin waxes (such as a carboxylic acid-terminated polyethylene wax or a carboxylic acid-terminated polypropylene wax); Fischer-Tropsch wax; ester waxes obtained from higher fatty acid and higher alcohol, such as stearyl stearate and behenyl behenate; ester waxes obtained from higher fatty acid and monovalent or multivalent lower alcohol, such as butyl stearate, propyl oleate, glyceride monostearate, glyceride distearate, and pentaerythritol tetrabehenate; ester waxes obtained from higher fatty acid and multivalent alcohol multimers, such as diethylene glycol monostearate, dipropylene glycol distearate, diglyceryl distearate, and triglyceryl tetrastearate; sorbitan higher fatty acid ester waxes, such as sorbitan monostearate, and cholesterol higher fatty acid ester waxes, such as cholesteryl stearate. Examples of functionalized waxes that may be used include, for example, amines, amides, for example AQUA SUPERSLIP 6550™, SUPERSLIP 6530™ available from Micro Powder Inc., fluorinated waxes, for example POLYFLUO 190™, POLYFLUO 200™, POLYSILK 9™, POLYSILK14™ available from Micro Powder Inc., mixed fluorinated, amide waxes, such as aliphatic polar amide functionalized waxes; aliphatic waxes consisting of esters of hydroxylated unsaturated fatty acids, for example MICROSPERSION 19™ also available from Micro Powder Inc., imides, esters, quaternary amines, carboxylic acids or acrylic polymer emulsion, for example JONCRYL 74™, 89™, 130™, 537™ and 538™, all available from SC Johnson Wax, and chlorinated polypropylenes and polyethylenes available from Allied Chemical and Petrolite Corporation and SC Johnson wax. Mixtures and combinations of the foregoing waxes may also be used in embodiments. Waxes may be included as, for example, fuser roll release agents. In embodiments, the waxes may be crystalline or non-crystalline.

In embodiments, the wax may be incorporated into the toner in the form of one or more aqueous dispersions of solid wax in water, where the solid wax particle size may be in the range of from about 100 to about 300 nanometers (nm).

In embodiments, the present toners are prepared by emulsion aggregation (EA) processes, such as by a process that includes aggregating a mixture of one or more emulsions, each emulsion comprising a resin; a fluorescent colorant or non-fluorescent colorant; and optionally a wax; and then coalescing the mixture. In embodiments, a crystalline polyester is provided, in embodiments in a separate emulsion. In embodiments, the crystalline polyester comprises C10:C9 polyester In embodiments, a process herein comprises combining one or more amorphous polyesters, water, and a fluorescent or non-fluorescent colorant to prepare a latex; optionally, adding an aggregating agent to the latex; heating the latex to form aggregated particles; adding a shell resin to the aggregated toner particles, the shell optionally comprising at least one amorphous polyester; and heating to coalesce the particles forming coalesced toner particles; and recovering the coalesced toner particles.

The mixture may be homogenized which may be accomplished by any suitable or desired process, such as by mixing at about 600 to about 6,000 revolutions per minute. Homogenization may be accomplished by any suitable means, including, for example, with an IKA ULTRA TURRAX T50 probe homogenizer.

Any suitable aggregating agent may be utilized in the process. Suitable aggregating agents include, for example, aqueous solutions of a divalent agent may be, for example, an inorganic cationic aggregating agent such as a polyaluminum halide such as polyaluminum chloride (PAC), or the corresponding bromide, fluoride, or iodide; a polyaluminum silicate such as polyaluminum sulfosilicate (PASS); or a water soluble metal salt including aluminum chloride, aluminum nitrite, aluminum sulfate, potassium aluminum sulfate, calcium acetate, calcium chloride, calcium nitrite, calcium oxylate, calcium sulfate, magnesium acetate, magnesium nitrate, magnesium sulfate, zinc acetate, zinc nitrate, zinc sulfate, zinc chloride, zinc bromide, magnesium bromide, copper chloride, and copper sulfate; or combinations thereof. The aggregating agent may be added to the mixture at a temperature that is below the glass transition temperature ($T_g$) of the resin(s). The aggregating agent may be added to the mixture under homogenization.

The aggregating agent may be added to the mixture in any suitable or desired amount, in embodiments, in an amount of, for example, from about 0% to about 10% by weight of the resin, from about 0.2% to about 8% by weight of the resin, or from about 0.5% to about 5% by weight of the resin.

The particles of the mixture may be permitted to aggregate until a predetermined desired particle size is obtained. A predetermined desired size refers to the desired particle size to be obtained as determined prior to formation, and the particle size being monitored during the growth process until such particle size is reached. Samples may be taken during the growth process and analyzed, for example with a Coulter Counter, for volume average particle size. The aggregation thus may proceed by maintaining an elevated temperature, or slowly raising the temperature to, for example, in embodiments, from about 30° C. to about 100° C., in embodiments from about 30° C. to about 80° C., or in embodiments from about 30° C. to about 50° C. The temperature may be held for a period time of from about 0.5 hours to about 6 hours, or in embodiments from about hour 1 to about 5 hours, while stirring, to provide the aggregated particles. Once the predetermined desired particle size is reached, a shell may be added. The volume average particle size of the particles prior to application of a shell may be, for example, from about 3 micrometers (μm) to about 10 μm, in embodiments, from about 4 μm to about 9 μm, or from about 6 μm to about 8 μm.

Shell Resin.

After aggregation, but prior to coalescence, a resin coating may be applied to the aggregated particles to form a shell thereover. Any of the resins described above may be utilized in the shell. In embodiments, an amorphous polyester resin is utilized in the shell. In embodiments, the shell comprises a first amorphous polyester and a second amorphous polyester. In embodiments, the shell comprises a first amorphous polyester and a second amorphous polyester and is free of other resins. In embodiments, two amorphous polyester resins are utilized in the shell, e.g., in substantially equal amounts. In embodiments, a crystalline polyester resin and two different types of amorphous polyester resins are utilized in the core and the same two types of amorphous polyester resins are utilized in the shell.

In certain embodiments, the shell comprises a first amorphous polyester comprising a poly(propoxylated bisphenol-co-terephthalate-fumarate-dodecenylsuccinate) and a second amorphous polyester comprising a poly(propoxyated-ethoxylated bisphenol-co-terephthalate-dodecenylsuccinate-trimellitic anhydride).

The shell may be applied to the aggregated particles by using the shell resins in the form of emulsion(s) as described above. Such emulsions may be combined with the aggregated particles under conditions sufficient to form a coating over the aggregated particles. For example, the formation of the shell over the aggregated particles may occur while heating to a temperature of from about 30° C. to about 80° C. or from about 35° C. to about 70° C. The formation of the shell may take place for a period of time from about 5 minutes to about 10 hours or from about 10 minutes to about 5 hours.

Once the desired size of the toner particles is achieved, the pH of the mixture may be adjusted with a pH control agent, a base, to a value of from about 3 to about 10, or in embodiments from about 5 to about 9. The adjustment of the pH may be utilized to freeze, that is to stop, toner growth. The base utilized to stop toner growth may include any suitable base such as, for example, alkali metal hydroxides such as, for example, sodium hydroxide, potassium hydroxide, ammonium hydroxide, combinations thereof, and the like. In embodiments, a chelating agent such as ethylene diamine tetraacetic acid (EDTA) may be added to help adjust the pH to the desired values noted above. Other chelating agents may be used.

In embodiments, the size of the core-shell toner particles (prior to coalescence) may be from about 3 µm to about 10 µm, from about 4 µm to about 10 µm, or from about 6 µm to about 9 µm.

Coalescence.

Following aggregation to the desired particle size and application of the shell, the particles may then be coalesced to the desired final shape, the coalescence being achieved by, for example, heating the mixture to a temperature of from about 45° C. to about 150° C., from about 55° C. to about 99° C., or about 60° C. to about 90° C., which may be at or above the glass transition temperature of the resins utilized to form the toner particles. Heating may continue or the pH of the mixture may be adjusted (e.g., reduced) over a period of time to reach the desired circularity. The period of time may be from about 1 hours to about 5 hours or from about 2 hours to about 4 hours. Various buffers may be used during coalescence. The total time period for coalescence may be from about 1 to about 9 hours, from about 1 to about 8 hours, or from about 1 to about 5 hours. Stirring may be utilized during coalescence, for example, from about 20 rpm to about 1000 rpm or from about 30 rpm to about 800 rpm.

After aggregation and/or coalescence, the mixture may be cooled to room temperature. The cooling may be rapid or slow, as desired. A suitable cooling process may include introducing cold water to a jacket around the reactor. After cooling, the toner particles may be screened with a sieve of a desired size, filtered, washed with water, and then dried. Drying may be accomplished by any suitable process for drying including, for example, freeze-drying.

Other Additives.

In embodiments, the present toners may also contain other optional additives. For example, the toners may include positive or negative charge control agents. Surface additives may also be used. Examples of surface additives include metal oxides such as titanium oxide, silicon oxide, aluminum oxides, cerium oxides, tin oxide, mixtures thereof, and the like; colloidal and amorphous silicas, such as AEROSIL®, metal salts and metal salts of fatty acids such as zinc stearate, calcium stearate, and magnesium stearate, mixtures thereof and the like; long chain alcohols such as UNILIN™ 700; and mixtures thereof.

Each of these surface additives may be present in an amount of from about 0.1% to about 5% by weight of the toner or from about 0.25% by weight to about 3% by weight of the toner. In embodiments, the toner may comprise, for example, from about 0.1% to about 5% of titania by weight of the toner, from about 0.1% to about 8% of silica by weight of the toner, from about 0.1% to about 5% of colloidal silica by weight of the toner, from about 0.05% to about 4% of zinc stearate by weight of the toner, and from about 0.1% to about 4% of cerium oxide by weight of the toner.

Developers and Carriers.

The present toners may be formulated into a developer composition. Developer compositions can be prepared by mixing the toners of the present disclosure with known carrier particles, including coated carriers, such as steel, ferrites, and the like. Such carriers include those disclosed in U.S. Pat. Nos. 4,937,166 and 4,935,326, the entire disclosures of each of which are incorporated herein by reference.

The toners may be present in the carrier in amounts of from about 1% to about 15% by weight, from about 2% to about 8% by weight, or from about 4% to about 6% by weight. The carrier particles can also include a core with a polymer coating thereover, such as polymethylmethacrylate (PMMA), having dispersed therein a conductive component like conductive carbon black. Carrier coatings include silicone resins such as methyl silsesquioxanes, fluoropolymers such as polyvinylidene fluoride, mixtures of resins not in close proximity in the triboelectric series such as polyvinylidene fluoride and acrylics, thermosetting resins such as acrylics, mixtures thereof and other known components.

Applications.

The present toners may be used in a variety of xerographic processes and with a variety of xerographic printers. A xerographic imaging process includes, for example, preparing an image with a xerographic printer comprising a charging component, an imaging component, a photoconductive component, a developing component, a transfer component, and a fusing component. In embodiments, the development component may include a developer prepared by mixing a carrier with any of the toners described herein. The xerographic printer may be a high-speed printer, a black and white high-speed printer, a color printer, and the like. Once the image is formed with the toners/developers, the image may then be transferred to an image receiving medium such as paper and the like. Fuser roll members may be used to fuse the toner to the image-receiving medium by using heat and pressure. Use of the present toners with a xerographic printing process can provide fluorescent printed images having the characteristics described herein including the brightness and L* a* b* coordinate values described herein.

The present toners find use in other applications such as powder coating applications in which a powder spray gun (e.g., a tribo gun) containing any of the present toners is used to deliver the toner to a substrate.

In embodiments, provided herein is a process for printing the fluorescent toner and the non-fluorescent toner at once using one or more of a combination of the Xerox® iGen® Press, in embodiments, the Xerox® iGen® 5 Press, the Xerox® iGen® Press. The sun exposure sensor is printed with a fluorescent toner. The sun exposure scale is printed with a non-fluorescent toner.

Thus a process herein is provided for preparing a sun exposure sensor using a fluorescent toner and a non-fluorescent toner. In embodiments, a process for preparing a sun exposure sensor comprises: providing a substrate having an upper surface and a lower surface; disposing a sun exposure sensing portion on the upper surface of the substrate, the sun exposure sensing portion comprising a fluorescent toner image, wherein the fluorescent toner image increasingly fades upon exposure to sunlight; disposing a sun exposure scale on the upper surface of the substrate, the sun exposure scale comprising an evaluation image for evaluating an amount of fading of the fluorescent toner image; optionally, disposing a coating layer over all or a portion of the upper surface of the substrate; optionally, disposing a backing layer disposed over all or a portion of the lower surface of the substrate.

In embodiments, disposing comprises using a xerographic printer to print one or more of the fluorescent toner image, the sun exposure evaluation image, the optional coating layer, and the optional backing layer.

In embodiments, disposing comprises using a xerographic printer in an inline process to print one or more of the fluorescent toner image, the sun exposure evaluation image, the optional coating layer, and the optional backing layer.

Any suitable substrate, recording sheet, or removable support, stage, platform, and the like, can be employed for preparing the sun exposure sensors herein, including plain papers such as XEROX® 4024 papers, XEROX® Image Series papers, Courtland 4024 DP paper, ruled notebook paper, bond paper, silica coated papers such as Sharp Company silica coated paper, JuJo paper, HAMMERMILL LASERPRINT® paper, and the like, glossy coated papers such as XEROX® Digital Color Gloss, Sappi Warren Papers LUSTROGLOSS®, and the like, transparency materials, fabrics, textile products, plastics, polymeric films, glass, glass plate, inorganic substrates such as metals and wood, as well as meltable or dissolvable substrates, such as waxes or salts, in the case of removable supports for free standing objects, and the like. In certain embodiments, the substrate is selected from the group consisting of paper, plastic, polymeric film, cardboard, paperboard, folded paperboard, Kraft paper, fabric, glass, glass plate, wood, metal, and combinations thereof. In embodiments, the substrate is a label. The label can be selected from any of the aforementioned types of substrate. In embodiments, the substrate comprises food packaging, medicinal packaging, and the like. In embodiment, the substrate comprises a member of the group consisting of food packaging, medicinal packaging, medical devices, cosmetic packaging, cosmetic tools, cosmetic products, and combinations thereof. In further embodiments, the substrate comprises a wearable device, such as a wristband. In embodiments, the substrate comprises a wristband, an armband, an ankle band, a hat, a shirt, a pair of pants, a pair of shorts, a shoe, a sneaker, a patch, a scarf, a pair of gloves, a sticker on a surface of an object, a sticker on a surface of a golf club, a pair of glasses, or sunglasses, or a cell phone case. The sensor can be disposed on or made of part of any other item as suitable or desired.

The substrate can be any suitable or desired color including darker colors which absorb more energy and may accelerate fading or lighter colors. In certain embodiments, the substrate is a white substrate.

EXAMPLES

The following Examples are being submitted to further define various species of the present disclosure. These Examples are intended to be illustrative only and are not intended to limit the scope of the present disclosure. Also, parts and percentages are by weight unless otherwise indicated.

Toners were prepared using fluorescent colorants as follows.

Example 1

FY-O, Optic Yellow. Preparation of solvent yellow 160 incorporated amorphous polyester emulsion. A mixture of 240 grams of an amorphous polyester resin (propoxylated bisphenol A fumarate/terephthalate), and 4.9 grams of solvent yellow 160 was dissolved in a mixture of methyl-ethyl-ketone, isopropyl-alcohol and aqueous ammonia solution with a ratio of (145/48/40 grams) in a 2 L reactor at 50° C. Additional ammonia solution may be needed to completely neutralize the polyester resin. To this solution was added 320 grams deionized water containing surfactants (Calfax® DB-45 from Pilot Chemical Company) to form emulsion. The reactor was charged with a distillation column and the organic solvent was distilled off. Finally, the resulting emulsion was filtered through a 25 µm sieve. The emulsion had an average particle size of 203 nanometers, and the solids content was about 41%. The solvent yellow 160 content in the emulsion was about 2%.

Example 2

FP49-M. A magenta polyester emulsion was prepared in the same way as the solvent yellow of Example 1, except that solvent red 49 magenta was used in place of solvent yellow 160.

Example 3

FP49-O, Optic. A polyester emulsion was prepared in the same way as the solvent yellow of Example 1, except that a mixture of solvent yellow 160 and solvent red 149 was used in place of solvent yellow 160.

Example 4

FP149-O, Optic. An orange polyester emulsion was prepared in the same way as the solvent yellow of Example 1, except that a mixture of solvent yellow 160 and solvent red 49 was used in place of solvent yellow 160.

Example 5

FB Blue. A blue polyester emulsion was prepared in the same way as the solvent yellow of Example 1, except that Pacific Blue or 3-carboxy-6,8-difluoro-7-hydroxycoumarin was used in place of solvent yellow 160.

Example 6

FG, Green. A green polyester emulsion was prepared in the same way as the solvent yellow of Example 1, except that a mixture of solvent yellow 160 and cyan pigment (PB 15:4) was used in place of solvent yellow 160.

Example 7

Preparation of fluorescent toner particles with solvent yellow 160 incorporated emulsion. The fluorescent emulsion made by Example 1 (225.2 grams) was mixed with one type of amorphous polyester emulsion (132.4 grams, 40% solid content), another type of amorphous polyester emulsion (132.4 grams, 40% solid content), another emulsion containing crystalline polyester (47.4 grams, 43% solid content) and deionized water (920.8 grams). After acidifying the mixture, aluminum sulfate solution was slowly added while homogenizing. The resulting highly viscous mixture was transferred into a 2 L reactor and the aggregation was initiated by increasing the temperature to about 45° C. When the particle size reached to 7.2 µm, emulsions including the two amorphous polyesters (107.2 grams, each) were added after acidification to pH 4.5 to form a shell over the particles and the particles were allowed to continue grow to about 8.5 µm. The particles were frozen by adding EDTA and sodium hydroxide aqueous solution. The reaction temperature was increased and coalescence started at about 84° C. The heating was stopped when the particle circularity reached 0.965±0.005. The particle slurry was quenched by lowering the temperature to below 40° C., then screened with 20-µm sieve, and filtered under vacuum. The resulting particles were washed with deionized water and dried.

Example 8

Preparation of fluorescent toner particles with FP49,M incorporated emulsion. Fluorescent toner particles were prepared as in Example 7, except that FP49,M emulsion of Example 2 was used.

Example 9

Preparation of fluorescent toner particles with FP49,Q-Optic incorporated emulsion. Fluorescent toner particles were prepared as in Example 7, except that FP49,Q-Optic emulsion of Example 3 was used.

Example 10

Preparation of fluorescent toner particles with FP1490,O-Optic incorporated emulsion. Fluorescent toner particles were prepared as in Example 7, except that FP1490,O-Optic emulsion of Example 4 was used.

Example 11

Preparation of fluorescent toner particles with FB Blue incorporated emulsion. Fluorescent toner particles were prepared as in Example 8, except that F0149, blue emulsion of Example 5 was used.

Example 12

Preparation of fluorescent toner particles with FG, Green incorporated emulsion. Fluorescent toner particles were prepared as in Example 8, except that FG, Green emulsion of Example 6 was used.

Lightfastness Investigation.

A series of images printed using the Xerox® iGen® and different fluorescent toners were lightfastness tested using Atlas CPS+Suntest® equipment. The fluorescent color toners tested were:

FY-O, Optic Yellow, Example 7.
FP49-M, Example 8.
FP49-O, Optic, Example 9.
FP149-O, Optic, Example 10.
FB, Blue, Example 11.
FG, Green, Example 12.

Figure 5:
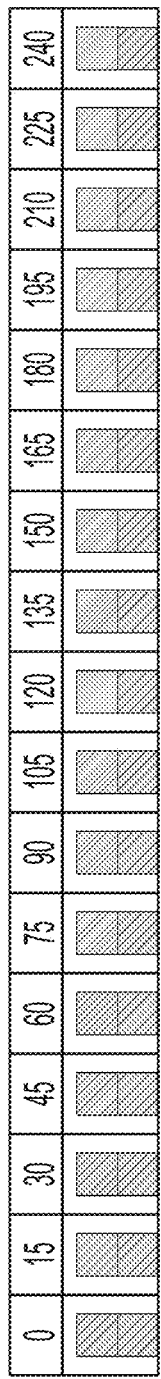
FIG. 5 is an illustration of a full sweep of sun exposure testing of a degrading patch (top row) and a non-degrading patch (bottom row).
Figure 6:
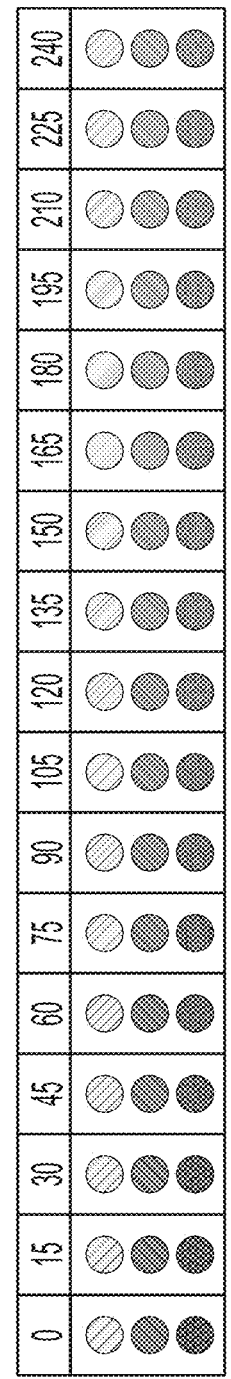
FIG. 6 is an illustration of a full sweep of sun exposure testing of three different toners that can be used to prepare a sensor in accordance with the present embodiments.

In embodiments, the printed sensor herein is prepared by printing a fluorescent toner on a substrate to form a solid image, and, next to the image, a sun exposure scale is printed with a regular pigmented toner simulating the color that the fluorescent toner progressively fades. The printed scale is robust to sunlight. The printed scale does not fade or has such minimal fade that it is negligible. The sensor portion printed with the fluorescent toner discolors when exposed to direct sunlight. The sun exposure level is easily found by comparing the amount of fade of the fluorescent toner image to the scale. In embodiments, the scale is numbered 0 to 8 illustrating progressive fade which correlates to fractions of an Arizona day. A printed scale can be made finer with a full sweep of sun exposure as shown in FIG. 5 and FIG. 6.

A color print comprising a solid image on a paper substrate was prepared with each of the fluorescent color toners of Examples 7-12 using a Xerox® iGen®.

The printed images were tested using Atlas CPS+Suntest® equipment. The testing conditions followed a 240 minute (4 hour) exposure in G155 mode. A color Lab was sampled for every 15 minutes of exposure.

Table 1 shows conditions for Pre-Set Tests G155 and 4892-1.

TABLE 1

| Pre-Set Tests | Filter | Reference Range (nm) | E W/m$^2$ | BST (° C.) |
|---|---|---|---|---|
| 1 | G155 | Daylight Reduced | 340 | 0.35 | 70 |
| 2 | 4892-1 | Daylight Reduced | 300-400 | 50 | 65 |

E W/m$^2$ = Irradiance (E) measured as watts per square meter
BST - black standard temperature.

Figure 4:
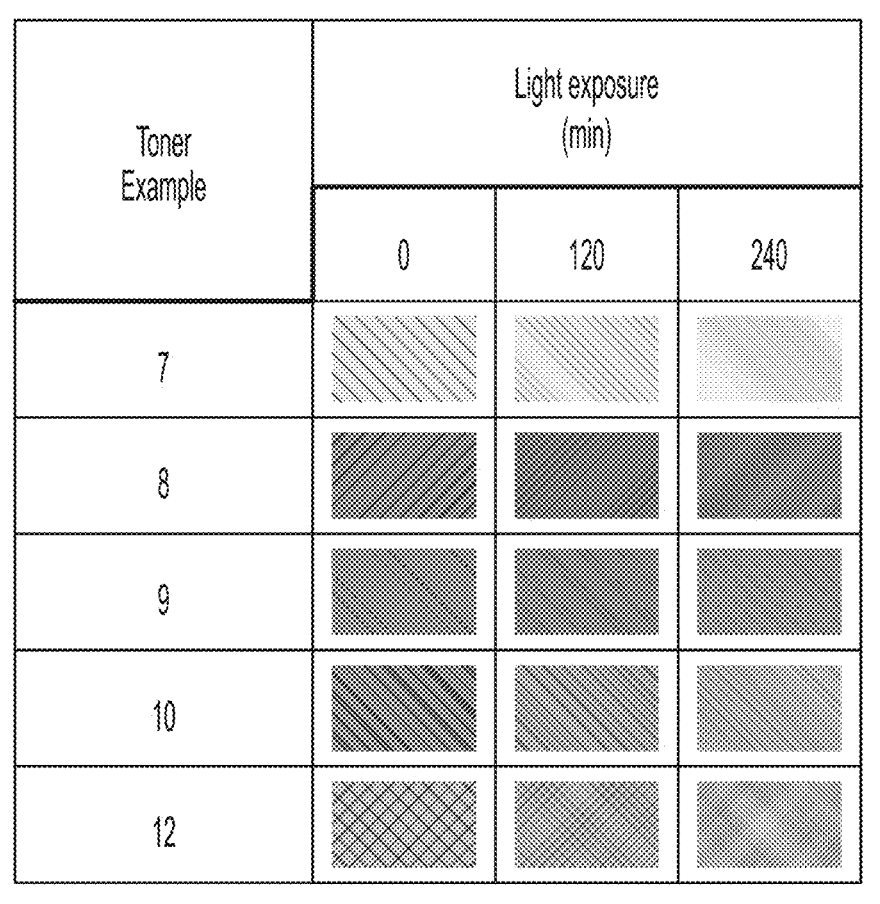

FIG. 4 illustrates the color change of fluorescent prints prepared with toner Examples 7, 8, 9, 10 and 12 under exposure time of 0, 120, and 240 minutes.

A full sweep of sun exposure with different color prints is shown in FIG. 5 and FIG. 6. In FIG. 5, top row, a degrading patch of a toner print made with FY-O, Optic Yellow, toner Example 7, is illustrated. In FIG. 5, bottom row, a non-degrading patch (bottom row) of a toner print made with a regular pigment CMYK toner which does not fade in sunlight is shown.

FIG. 6 illustrates three different toner formulations that can be used to build the sensor. In FIG. 6, top row, a printed patch of the optic yellow toner of Example 7 is shown from 0 to 240 minutes of exposure in accordance with the Atlas CPS+Suntest in G155 mode. In FIG. 6, middle row, a printed patch of the color toner of Example B is shown from 0 to 240 minutes of exposure. In FIG. 6, bottom row, a printed patch of the color toner of Example 10 is shown from 0 to 240 minutes of exposure.

Figure 7:
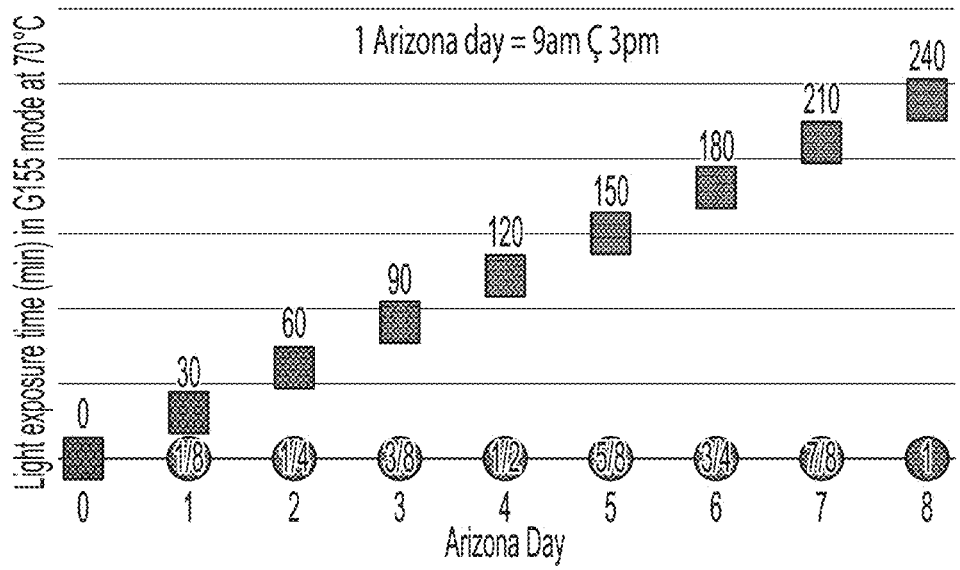
FIG. 7 is a graph illustrating light exposure time (minutes) in G155 mode at 70° C. of fluorescent orange toner with color change correlated to fractions of an Arizona Day.

FIG. 7 illustrates exposure time associated with the color change of a fluorescent orange toner print prepared with the toner of Example 10 correlated to fractions of an Arizona day.

Figure 8:
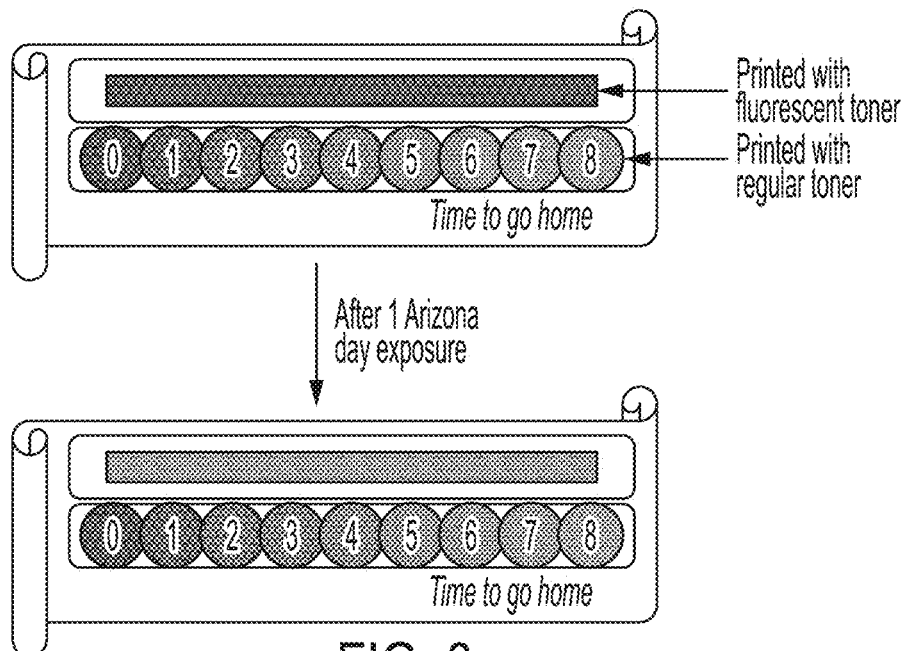
FIG. 8 is an illustration of a sun exposure sensor prepared in accordance with the present embodiments.

FIG. 8 illustrates a sun exposure sensor prepared with the fluorescent toner of Example 10 and a scale printed with a regular toner, Xerox® CMYK toner. A sensing strip was printed on to a substrate using the fluorescent toner of Example 10 using a Xerox® iGen®. A scale was printed adjacent to the fluorescent toner strip with non-fluorescent Xerox® toner. The scale including an image of successive numbered circles 0 to 8 of fading color intensity to indicate increasing sun exposure, with 0 being least exposure and 8 indicating the most exposure. After the equivalent of one Arizona day of sun exposure, as indicated by the arrow, the sensor strip changed color to match the faded scale color indicating the amount of sun exposure.

Thus, a single use, disposable sun exposure sensor is provided based on fluorescent toner prints. The sensor has a sun exposure scale indicating color change. The sensor can correlate the sun exposure to an Arizona day. The sensor is simple, easy to use, and inexpensive. The whole sun exposure sensor can be printed in a single pass print job and employ all of the features and advantages of the printing machine, from capability in many media types to various finishing operations. Compared to currently available disposable sensors, the present sensor is prepared with simpler materials and can be made robust against weather and scratch.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

The invention claimed is:

1. A sun exposure sensor for disposable or single use comprising:
   a substrate having an upper surface and a lower surface;
   a sun exposure sensing portion disposed on the upper surface of the substrate, the sun exposure sensing portion comprising a fluorescent toner image, wherein the fluorescent toner image increasingly fades upon exposure to sunlight; and
   a sun exposure scale disposed on the upper surface of the substrate, the sun exposure scale comprising an evaluation image for evaluating an amount of fading of the fluorescent toner image.

2. The sun exposure sensor of claim 1, wherein the substrate is selected from the group consisting of paper, plastic, polymeric film, cardboard, paperboard, folded paperboard, Kraft paper, fabric, glass, glass plate, wood, metal, and combinations thereof.

3. The sun exposure sensor of claim 1, wherein the substrate is white.

4. The sun exposure sensor of claim 1, wherein the sun exposure sensing portion fluorescent toner image is printed with a fluorescent toner covering a spectrum of reflectance from 400 nm to 700 nm.

5. The sun exposure sensor of claim 1, wherein the sun exposure sensing portion fluorescent toner image is printed with a fluorescent toner selected from the group consisting of yellow fluorescent toner, magenta fluorescent toner, orange fluorescent toner, pink fluorescent toner, green fluorescent, red fluorescent toner, blue fluorescent toner, and combinations thereof.

6. The sun exposure sensor of claim 1, wherein the sun exposure sensing portion is printed with a fluorescent yellow toner comprising:
   a core comprising a first solvent yellow 160-incorporated amorphous polyester; a second solvent yellow 160-incorporated amorphous polyester; wherein the first amorphous polyester and the second amorphous polyester are different; and a crystalline polyester;
   a shell disposed over the core, the shell comprising at least one amorphous polyester;
   wherein the toner provides printed images having an L* value of greater than 90, an a* value of from about less than −40 to about −20, and a b*value of greater than 75.

7. The sun exposure sensor of claim 1, wherein the sun exposure scale is printed with a non-fluorescent toner.

8. The sun exposure sensor of claim 1, further comprising: a coating layer disposed over all or a portion of the upper surface of the substrate wherein the coating layer comprises a water-resistant overcoat layer.

9. The sun exposure sensor of claim 1, further comprising: a coating layer disposed over all or a portion of the upper surface of the substrate wherein the coating layer comprises a scratch-resistant overcoat layer.

10. The sun exposure sensor of claim 1, wherein the sun exposure sensor further comprises a backing layer and wherein the backing layer comprises a hook and loop layer, an adhesive layer, a gel pad, or combinations thereof.

11. The sun exposure sensor of claim 1, wherein the substrate comprises a wearable device.

12. The sun exposure sensor of claim 1, wherein the substrate is a wristband, an armband, an ankle band, a hat, a shirt, a pair of pants, a pair of shorts, a shoe, a sneaker, a patch, a scarf, a pair of gloves, a sticker on a surface of an object, a sticker on a surface of a golf club, a pair of glasses, or sunglasses, or a cell phone case.

13. The sun exposure sensor of claim 1, further comprising:
   at least one of a coating layer disposed over all or a portion of the upper surface of the substrate, a backing layer disposed over all or a portion of the lower surface of the substrate, or a combination thereof.

14. A sun exposure sensor for disposable or single use comprising:
   a first substrate having an upper surface and a lower surface;
   a sun exposure sensing portion disposed on the upper surface of the first substrate, the sun exposure sensing portion comprising a fluorescent toner image, wherein the fluorescent toner image increasingly fades upon exposure to sunlight;
   a second substrate having an upper surface and a lower surface; and
   a sun exposure scale disposed on the upper surface of the second substrate, the sun exposure scale comprising an evaluation image for evaluating an amount of fading of the fluorescent toner image.

15. The sun exposure sensor of claim 14, further comprising:
   at least one of a coating layer disposed over all or a portion of the upper surface of the first substrate, a coating layer disposed over all or a portion of the upper surface of the second substrate, a backing layer disposed over all or a portion of the lower surface of the first substrate; a backing layer disposed over all or a portion of the lower surface of the second substrate, or a combination thereof.

16. A process for preparing a sun exposure sensor, the process comprising:
   providing a substrate having an upper surface and a lower surface;
   disposing a sun exposure sensing portion on the upper surface of the substrate, the sun exposure sensing portion comprising a fluorescent toner image, wherein the fluorescent toner image increasingly fades upon exposure to sunlight; and
   disposing a sun exposure scale on the upper surface of the substrate, the sun exposure scale comprising an evaluation image for evaluating an amount of fading of the fluorescent toner image.

17. The process of claim 16, wherein disposing comprises using a xerographic printer to print one or more of the fluorescent toner image, the sun exposure evaluation image; the optional coating layer, and the optional backing layer.

18. The process of claim 16, wherein disposing comprises using a xerographic printer in an inline process to print one or more of the fluorescent toner image, the sun exposure evaluation image; the optional coating layer, and the optional backing layer.

19. The process of claim 16, wherein the sun exposure sensing portion fluorescent toner image is printed with a fluorescent toner covering a spectrum of reflectance selected from 400 nm to 700 nm.

20. The process of claim 16, wherein the sun exposure sensing portion fluorescent toner image is printed with a fluorescent toner selected from the group consisting of yellow fluorescent toner, magenta fluorescent toner, orange fluorescent toner, pink fluorescent toner, green fluorescent, red fluorescent toner, blue fluorescent toner, and combinations thereof.

21. The process of claim 16, wherein the substrate is selected from the group consisting of paper, plastic, polymeric film, cardboard, paperboard, folded paperboard, Kraft paper, fabric, glass, glass plate, wood, metal, and combinations thereof.

22. The process of claim 16, wherein the substrate is white.

23. The process of claim 16, further comprising:
   disposing at least one of a coating layer over all or a portion of the upper surface of the substrate; a backing layer disposed over all or a portion of the lower surface of the substrate, or a combination thereof.

* * * * *